US007589054B2

(12) United States Patent
Ohlhausen et al.

(10) Patent No.: US 7,589,054 B2
(45) Date of Patent: Sep. 15, 2009

(54) CLATHRATES OF AN ORGANOSILANE QUATERNARY AMMONIUM COMPOUND AND UREA AND METHODS OF USE

(75) Inventors: Howard G. Ohlhausen, Paradise Valley, AZ (US); Jerome H. Ludwig, Sun City West, AZ (US)

(73) Assignee: Resource Development L.L.C., Scottsdale, AZ (US)

( * ) Notice: Subject to any disclaimer, the term of this patent is extended or adjusted under 35 U.S.C. 154(b) by 155 days.

(21) Appl. No.: 11/619,085

(22) Filed: Jan. 2, 2007

(65) Prior Publication Data

US 2008/0161219 A1 Jul. 3, 2008

(51) Int. Cl.
*C11D 3/00* (2006.01)
*A01N 55/00* (2006.01)
*B01D 21/01* (2006.01)
*B01J 13/00* (2006.01)
*C08J 3/02* (2006.01)

(52) U.S. Cl. .................. 510/504; 516/102; 514/63; 510/368; 510/391; 510/400; 510/528; 106/2; 106/287.11

(58) Field of Classification Search .................. 510/368, 510/391, 400, 504, 528; 106/2, 287.11; 514/63; 516/102
See application file for complete search history.

(56) References Cited

U.S. PATENT DOCUMENTS

| | | | |
|---|---|---|---|
| 2,612,458 A | 9/1952 | Stedman | |
| 2,923,653 A | 2/1960 | Matlin et al. | |
| 2,962,390 A | 11/1960 | Fain et al. | |
| 3,130,164 A | 4/1964 | Best | |
| 3,244,541 A | 4/1966 | Fain et al. | |
| 3,560,385 A | 2/1971 | Roth | |
| 3,579,540 A | 5/1971 | Ohlhausen | |
| 3,730,701 A | 5/1973 | Isquith et al. | |
| 3,794,736 A | 2/1974 | Abbott et al. | |
| 3,817,739 A | 6/1974 | Abbot et al. | |
| 3,860,709 A | 1/1975 | Abbott et al. | |
| 3,865,728 A | 2/1975 | Abbott et al. | |
| 4,005,025 A | 1/1977 | Kinstedt | |
| 4,005,028 A | 1/1977 | Heckert et al. | |
| 4,005,030 A | 1/1977 | Heckert et al. | |
| 4,161,518 A | 7/1979 | Wen et al. | |
| 4,259,103 A | 3/1981 | Malek et al. | |
| 4,282,366 A | 8/1981 | Eudy | |
| 4,311,598 A | 1/1982 | Verachtert | |
| 4,361,273 A | 11/1982 | Levine et al. | |
| 4,390,712 A | 6/1983 | Karl et al. | |
| 4,394,378 A | 7/1983 | Klein | |
| 4,397,757 A | 8/1983 | Bright et al. | |
| 4,406,892 A | 9/1983 | Eudy | |
| 4,421,796 A | 12/1983 | Burril et al. | |
| 4,430,236 A | 2/1984 | Franks | |
| 4,467,013 A | 8/1984 | Baldwin | |
| 4,557,854 A | 12/1985 | Plueddemann | |
| 4,567,039 A | 1/1986 | Stadnick et al. | |
| 4,576,728 A | 3/1986 | Stoddart | |
| 4,615,882 A | 10/1986 | Stockel | |
| 4,631,273 A | 12/1986 | Blehm et al. | |
| 4,682,992 A | 7/1987 | Fuchs | |
| 4,781,974 A | 11/1988 | Bouchette et al. | |
| 4,797,420 A | 1/1989 | Bryant | |
| 4,835,019 A | 5/1989 | White et al. | |
| 4,842,766 A | 6/1989 | Blehm et al. | |
| 4,845,256 A | 7/1989 | Mebes et al. | |
| 4,847,088 A | 7/1989 | Blank | |
| 4,866,192 A | 9/1989 | Plueddemann et al. | |
| 4,941,989 A | 7/1990 | Kramer et al. | |
| 4,990,377 A | 2/1991 | Wilson | |
| 4,999,249 A | 3/1991 | Deschler et al. | |
| 5,013,459 A | 5/1991 | Gettings et al. | |
| 5,209,775 A | 5/1993 | Bank et al. | |
| 5,320,805 A | 6/1994 | Kramer et al. | |
| 5,348,556 A | 9/1994 | Minns et al. | |
| 5,360,568 A | 11/1994 | Madison et al. | |
| 5,360,569 A | 11/1994 | Madison et al. | |
| 5,411,585 A * | 5/1995 | Avery et al. ............... | 106/287.1 |
| 5,426,204 A | 6/1995 | Harisiades et al. | |
| 5,478,357 A | 12/1995 | Madison et al. | |
| 5,552,476 A | 9/1996 | Halling | |
| 5,620,527 A | 4/1997 | Kramer et al. | |

(Continued)

FOREIGN PATENT DOCUMENTS

CA 1010782 5/1977

(Continued)

OTHER PUBLICATIONS

STIC search results, see pdf.*

(Continued)

*Primary Examiner*—Mark Eashoo
*Assistant Examiner*—Jane L Stanley
(74) *Attorney, Agent, or Firm*—Wood, Herron & Evans LLP

(57) ABSTRACT

Storage-stable organosilane quaternary compounds are provided in the form of adducts with urea (clathrates). The urea-organosilane quaternary clathrates enable the shipment, storage and preparation of compositions without hazardous solvents for end-use by manufacturers and consumers. Multifunctional cleansing and coating compositions are prepared employing the clathrates without sacrificing the properties and benefits of the organosilane quats.

52 Claims, No Drawings

U.S. PATENT DOCUMENTS

| | | | |
|---|---|---|---|
| 5,705,690 A * | 1/1998 | Varadaraj et al. | 564/1.5 |
| 5,798,144 A | 8/1998 | Varanasi et al. | |
| 5,885,951 A | 3/1999 | Loder | |
| 5,954,869 A | 9/1999 | Elfersy et al. | |
| 5,959,014 A | 9/1999 | Liebeskind et al. | |
| 6,051,730 A * | 4/2000 | Pallas et al. | 556/419 |
| 6,060,522 A * | 5/2000 | Pallas et al. | 516/102 |
| 6,087,319 A | 7/2000 | Norman | |
| 6,113,815 A | 9/2000 | Elfersy et al. | |
| 6,120,587 A | 9/2000 | Elfersy et al. | |
| 6,218,351 B1 | 4/2001 | Busch et al. | |
| 6,221,944 B1 | 4/2001 | Liebeskind et al. | |
| 6,240,929 B1 | 6/2001 | Richard et al. | |
| 6,309,425 B1 | 10/2001 | Murphy | |
| 6,316,399 B1 | 11/2001 | Melikyan et al. | |
| 6,346,279 B1 | 2/2002 | Rochon | |
| 6,361,787 B1 | 3/2002 | Shaheen et al. | |
| 6,372,702 B1 | 4/2002 | Chiou et al. | |
| 6,376,448 B1 * | 4/2002 | Colurciello et al. | 510/384 |
| 6,391,840 B1 | 5/2002 | Thompson et al. | |
| 6,403,547 B1 | 6/2002 | Grippaudo et al. | |
| 6,417,151 B1 | 7/2002 | Grothus et al. | |
| 6,432,181 B1 | 8/2002 | Ludwig | |
| 6,436,445 B1 | 8/2002 | Hei et al. | |
| 6,461,537 B1 | 10/2002 | Turcotte et al. | |
| 6,528,472 B2 | 3/2003 | Charaf et al. | |
| 6,530,384 B1 | 3/2003 | Meyers et al. | |
| 6,534,075 B1 | 3/2003 | Hei et al. | |
| 6,548,467 B2 | 4/2003 | Baker et al. | |
| 6,559,111 B2 | 5/2003 | Colurciello, Jr. et al. | |
| 6,610,777 B1 | 8/2003 | Anderson et al. | |
| 6,613,755 B2 | 9/2003 | Peterson et al. | |
| 6,676,733 B2 | 1/2004 | Ludwig et al. | |
| 6,740,626 B2 | 5/2004 | Neumiller | |
| 6,762,172 B1 * | 7/2004 | Elfersy et al. | 514/63 |
| 6,809,072 B2 | 10/2004 | Abidh et al. | |
| 6,881,247 B2 | 4/2005 | Batdorf | |
| 6,897,191 B2 | 5/2005 | Batdorf | |
| 6,994,890 B2 | 2/2006 | Ohlhausen et al. | |
| 7,151,139 B2 | 12/2006 | Tiller et al. | |
| 7,183,434 B2 | 2/2007 | Baan et al. | |
| 2002/0026881 A1 * | 3/2002 | Ludwig et al. | 106/2 |
| 2005/0089695 A1 | 4/2005 | Moffat et al. | |
| 2005/0096250 A1 * | 5/2005 | Ohlhausen et al. | 510/504 |
| 2006/0110348 A1 | 5/2006 | Ohlhausen et al. | |
| 2007/0010419 A1 * | 1/2007 | Ohlhausen et al. | 510/368 |

FOREIGN PATENT DOCUMENTS

| | | |
|---|---|---|
| CA | 1217004 | 1/1987 |
| DE | 19538629 A1 | 4/1997 |
| EP | 0051823 A1 | 5/1982 |
| EP | 0129980 A1 | 1/1985 |
| WO | WO 9732957 A | 9/1997 |
| WO | 00/54587 A1 | 9/2000 |
| WO | 00/72850 A1 | 12/2000 |

OTHER PUBLICATIONS

Chapoy et al. J. Am. Chem. Soc. 2007, 129, 746-747 "Low-Pressure Molecular Hydrogen Storage in Semi-clathrate Hydrates of Quaternary Ammonium Compounds".*

Wiebcke et al. J. Chem. Soc., Chem. Commun. 1993, 1604-1606 "Structural Links between Zeolite-type and Clathrate Hydrate-type Materials".*

Cadwallader, D.E. et al, "Inclusion compounds of urea and thiourea with cationic surfactants"; Database CA [Online] Chemical Abstracts Service, Columbus, Ohio, US. XP002477047 retrieved from STN; Database accession No. 1965:83521 (Abstract Only).

Ivanova, E. B., "Disinfecting agent Veltab as tablet"; Database CA [Online] Chemical Abstracts Service, Columbus, Ohio, US. XP002477048 retrieved from STN Database accession No. 2003:918985 (Abstract Only); And RU 2,214,837 C1 (Russia).

European Search Report for European Patent Application 07254915.7.

International (PCT) Search Report and Written Opinion for PCT Application US2007/080157.

Radell et al., Occlusion of Organosilanes by Urea, Journal of the American Chemical Society, vol. 80, pp. 2683-2685 (1958).

* cited by examiner

CLATHRATES OF AN ORGANOSILANE QUATERNARY AMMONIUM COMPOUND AND UREA AND METHODS OF USE

FIELD OF THE INVENTION

This invention relates to a clathrate of an organosilane quaternary ammonium compound ("organosilane quat") and urea. The clathrates are made by a number of different methods including crystallization, dry mixing of components, or concentration. The clathrates are storage-stable and provide a useful form of the organosilane quaternary compounds and urea for shipping, handling and concentrating the components in solid form for various end uses including cleansing and multifunctional coating compositions with antimicrobial properties. The cleansing and multicoating compositions yield invisible, but durable water, soil and stain repellant barrier coatings when applied to siliceous, plastic, metal, textile and skin surfaces.

BACKGROUND OF THE INVENTION

Organosilane quaternary nitrogen compounds have been employed effectively for imparting water, soil and stain repellency and reducing and/or eliminating microbial contamination when applied to a variety of surfaces. For instance, bacterial, viral and fungal contamination may be reduced or eliminated when such organosilane quaternary compounds are applied to surfaces. Commercially available quaternary ammonium organosilanes which have been used for this purpose include 3-(trimethoxysilyl)propyidimethyloctadecyl ammonium chloride, 3-(trimethoxysilyl)propyldidecylmethyl ammonium chloride, and 3-(trimethoxysilyl)propyltetradecyidimethyl ammonium chloride. The following patents and patent applications disclose the use of siliconized and/or non-siliconized quaternaries, solvents and surfactants/detergents for the cleaning and/or water repellent treatment of substrates: U.S. Pat. Nos. 4,005,028; 4,005,030; 6,559,111; 6,897,191; 6,809,072; U.S. Publ. No. 2005/0089695; U.S. Publ. No. 2005/0020474; U.S. Publ. No. 2003/0109395; U.S. Pat. No. 6,881,247; U.S. Publ. No. 2003/0091641 and U.S. Pat. No. 5,426,204.

Many different types of hard and soft surfaces have also been cleaned of soluble soil, provided with a water and soil repellent finish and rendered antimicrobial by coating with different agents. For example, U.S. Pat. No. 6,994,890, which issued on Feb. 7, 2006 (Ohlhausen and Ludwig), discloses a "Cleaning and Multifunctional Coating Composition Containing An Organosilane Quaternary Compound and Methods of Using" from aqueous systems with hydrogen peroxide. Such compositions are exceptionally effective in removing water and oil soluble soil from surfaces while simultaneously providing a water and soil repellent barrier coating for easier cleaning and to reduce microbial contamination.

Further improvements in surfactant-free storage-stable liquid cleansing and multifunctional coating compositions to satisfactorily or completely remove insoluble buildup have been made with reference to U.S. application Ser. No. 11/175,583, filed Jul. 6, 2005, entitled, "A Surfactant-Free Cleansing and Multifunctional Liquid Coating Composition Containing Nonreactive Abrasive Solid Particles and An Organosilane Quaternary Compound and Methods of Using (Ohlhausen and Ludwig). Because of the reactivity of the organosilane quat, it is employed with nonreactive abrasive solid particles to cleanse insoluble surface soil and simultaneously impart a water, soil and stain repellant barrier coating.

Thus, organosilane quats are among the world's most flexible, thin-film surface modifying compounds. They are substantive to hard and soft substrates alike. They yield invisible, but durable, water, soil and stain repellent barrier coatings when applied to siliceous, plastic, metal, skin, and textile surfaces from water-based compositions.

However, the chemical nature and structure of quats are such that they are highly reactive, but not storage-stable. They are inherently subject to condensation and cross-linking until they are extensively diluted and/or compounded with compatible additives. Also, organosilane quats are typically offered by their manufacturers in concentrations of 40-72% in methanol and other solvents, which are flammable, toxic and poisonous. Moreover, as such concentrated quats age, their viscosities, appearance, color and compounding ability vary significantly.

For all of the far-reaching performance benefits of organosilane quats, their relative lack of storage stability, handling and shipping hazards, until extensively diluted to make them economically viable, have limited their formulation and sales prospects. Thus, there is a clear need for storage-stable, non-flammable forms of organosilane quats. There is a particular need for them in concentrations that can be readily formulated by manufacturers and end-users alike into a variety of surface care products where the residual water, soil and stain repellent characteristics of the organosilane quats offer desirable properties and benefits. Examples of such products range from windscreen washer fluids and glass cleaners to multifunctional cleaners and antimicrobial barrier coatings.

SUMMARY OF THE INVENTION

This invention is directed to new clathrate(s) of urea and an organosilane quaternary ammonium compound.

The clathrates are storage-stable solids that can be used "as is" or readily and broadly formulated by manufacturers and end users into a variety of products. Surprisingly, it has been found that urea interacts with organosilane quats to form solid clathrates and provide a new, storage-stable, non-flammable, non-toxic form of the organosilane quat.

Accordingly, the urea-organosilane quat clathrates solve a number of problems presently confronting utilization of the otherwise highly reactive quats. The clathrate form of the urea-organosilane quats overcomes the problems of lack of storage stability, handling and shipping hazards associated with existing quats. Moreover, the non-flammable form of the clathrate organosilane quat overcomes the current problems associated with manufactured products that exist in 40%-72% concentrations in methanol, which is a flammable, hazardous and poisonous solvent. The clathrate form of the urea-organosilane quats can be readily formulated by manufacturers and end users into a variety of surface care, skin care and textile care products where the residual water, soil and stain repellent characteristics of the quats offer desirable properties and benefits. It has been found that various concentrations, up to 25%, of different organosilane quats can be blended with urea to form clathrates which can be stored in sealed or unsealed glass jars, plastic bottles or containers and paper envelopes for periods of up to several months and years without any apparent loss or change in color, texture or agglomeration. When these products were applied as powders to the surfaces indicated, and moistened, they cleaned the surface and provided a water, soil and stain repellent barrier coating. When these products were charged into containers of deionized water and stirred, the resulting mixtures were clear, water white and free of particulates that would normally be associated with cross-linked or reacted quats. By comparison, quantities of ordinary non-urea organosilane quats, stored in a similar manner for comparable terms, had congealed and condensed. When ordinary organosilane quats were stirred into the deionized water, they dissolved slowly and yielded mixtures that usually became cloudy and contained floating quat-derived particulates.

It has also been found that the storage-stable clathrates of this invention can be diluted with various diluents and still maintain their storage stabilities. This discovery is important from a commercial standpoint because the organosilane quats are relatively expensive and it would be desirable to provide diluted concentrates and other storage-stable forms of the clathrates, which may then be used by manufacturers and end users. In one preferred form of the invention, the clathrates are diluted with urea to provide storage-stable solids. In other forms, the clathrate may be diluted with a surfactant, thickener, gelling agent, abrasive, lubricant, urea peroxide, and/or polyvinyl pyrrolidone peroxide, among other solids. The clathrates may also be diluted with water, an alcohol, and mixtures thereof, especially in end-use products where the active organosilane quat is released from the clathrate to serve its useful functions. In a preferred form of the clathrate, urea is readily and completely water soluble. When so solubilized, it lowers the surface tension of water, allows the water-urea composition to better penetrate a wide range of organic and inorganic soil on surfaces when compared to water without urea. In the clathrate form of urea-organosilane quat, when urea is solubilized in water, or water and alcohol, the resulting composition is likewise more surface-active and provides improved cleaning and bonding of the organosilane quat to the surface than would the same level of organosilane quat in water without urea.

It has also been found that compositions of the urea-organosilane clathrate, containing additional urea as a diluent for the clathrate, significantly aids in the removal of various types of organic and inorganic soil without scratching the surfaces that are so treated. In this form of the invention, the composition of the clathrate utilizes the abrasive property of various solid forms of urea. Surprisingly, the powdered clathrate of urea-organosilane quat not only cleans the surface as a mild abrasive, but simultaneously imparts a water, soil, and stain repellent barrier coating with improved bonding owing, it is believed, to a synergistic combination of the surface tension reducing and abrasive attributes of the mixture. Thus, the abrasive properties of the clathrate that has been diluted with urea may be modified, depending upon the amount of abrasive urea in the composition. In this regard, a still further benefit of the invention is the finding that, unlike the water-insoluble nature of a broad range of mineral abrasives typically employed in cleansers, the urea-type abrasive is 100% water soluble and, thus, easily and quickly rinsed off a clean surface without leaving a gritty residue and without adding water insoluble particles to the waste water system.

These and other benefits of the compositions and methods of this invention will be further understood with reference to the following detailed description.

DETAILED DESCRIPTION

This invention is concerned with urea clathrates or adducts of organosilane quats. These quats are also referred to hereinafter as siliconized quaternary compounds. While it is well known that urea forms clathrate or adducts (inclusion complexes) with a large number of linear organic compounds, the formation of clathrates is unpredictable. Urea can form a different crystal lattice in the presence of long chain organic molecules, which contains hexagonal channels formed by spirally coiled urea molecules (like a pipe) that are about 5-6 angstroms in diameter. The long chain guest molecules are positioned inside the coiled urea molecules of the adduct crystal. A carbon chain length of 8 to 9 carbons is generally regarded as the minimum length for the guest molecules to form stable urea adducts. The adduct crystal can be thought of as a pile of pipe (the pipe being the coiled urea molecules) with the guest molecules inside the pipe.

In the case of this invention, for reasons more detailed hereinafter, the structure of the inventive urea-organosilane quats would not have been obvious to a person of ordinary skill in the art. It has been found that the methoxylated organosilane quaternary compounds, having linear hydrocarbon chain lengths of 10 to 22 carbons, are sufficient to form urea adducts or clathrates. In this form, the organosilane quaternary compounds are chemically stabilized within the enclosed urea pipe structure and are therefore inhibited from degradation or polymerization with each other. The shelf life or storage stability of the organosilane quaternary compound is therefore improved substantially, even indefinitely.

Organosilane Quaternary Compounds of this Invention

The organosilane quaternary compounds of this invention are defined by the formula:

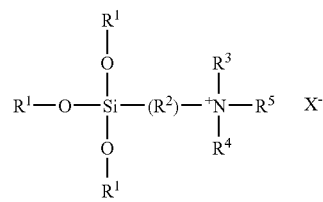

Wherein $R^1$=hydrogen and/or $C_1$ to $C_4$ alkyl; $R^2$=divalent hydrocarbon radical with $C_1$ to $C_8$ carbon atoms, $R^3$=hydrogen or $C_1$ to $C_4$ alkyl, $R^4$=hydrogen or $C_1$ to $C_{10}$ alkyl, $R^5$=$C_{10}$ to $C_{22}$ saturated or unsaturated hydrocarbon radical and X=halide, carboxylate, sulfonate, hydroxide, sulfate, or phosphate. Typical organosilane quaternary compounds are selected from the group consisting of:

3-(trimethoxysilyl)propyldimethyloctadecyl ammonium chloride, 3-(trimethoxysilyl)propyldidecylmethyl ammonium chloride, 3-(trimethoxysilyl)propyltetradecyidimethyl ammonium chloride, 3-(trimethoxysilyl)propyldimethylsoya ammonium chloride, 3-(trimethoxysilyl)propyldimethyloleyl ammonium chloride, 3-(trimethoxysilyl)propyloctadecyl ammonium chloride, 3-(trimethoxysilyl)propyloleyl ammonium chloride, 3-(trihydroxysilyl)propyldimethyloctadecyl ammonium chloride, and 3-(trimethoxysilyl)propyldocosane ammonium chloride.

With the discovery of clathrates of the above type organosilane quats, it will be appreciated that other similar organosilane quats will form clathrates with urea, notwithstanding the general unpredictability of clathrate formation in the field of art.

Notwithstanding the rather complex structure of the above quats, it has been found that, when the organosilane quat has at least one linear chain of at least 10 carbon atoms, the clathrate adduct with urea, surprisingly, is formed. The linear hydrocarbon chain length is preferably from 10 to 22 carbons, and the hydrocarbon group is a $C_{10}$-$C_{22}$ saturated or unsaturated hydrocarbon group. In the clathrate form of the inventive composition, the organosilane quaternary compound is present in an amount up to about 25% by weight of the clathrate. The organosilane quat may vary in an amount of from about 1% to about 25% by weight of the clathrate. When the powdered or solid clathrate is diluted with water, or an alcohol, and mixtures thereof, the urea and the organosilane quat are released from the clathrate to provide a variety of surface care products where the residual water, soil and stain repellent characteristics of the organosilane quats offer desirable properties and benefits. Examples of such products range from windscreen washer fluids and glass cleaners to multifunctional cleaners, cleansers, and antimicrobial barrier coating compositions.

Typically, when diluted with water, the clathrates generally yield up to about 5% by weight of the organosilane quat based upon the total weight of the clathrate and diluent. Concentrations of the quat of about 0.01 to about 1% by weight in water yield useful products. The clathrate compositions of this invention may also be used in their solid form because it has been found, surprisingly, that such solids, when rubbed onto surfaces in the presence of moisture yield water, soil and stain repellent barrier coatings. The released quat provides a barrier coating and the urea acts as an abrasive during cleaning, which then may be solubilized for removal from the surface. A major advantage provided by the solid clathrates of this invention enables the urea-organosilane quat to be storage-stable. More preferably, end-use liquid compositions containing hydrogen peroxide or a complex thereof in amounts of from about 3 to about 6% by weight, and quaternary compound amounts of about 0.01 to about 1% by weight are employed.

Wherefore, the invention enables the preparation of storage-stable cleansing and multifunctional coating compositions for treating a surface thereby rendering it water and soil repellent. The end-use composition can contain abrasive particles, and can be formulated as a slurry, cream, gel, or powder. Moreover, the clathrate may be combined with additives selected from the group consisting of urea, a surfactant, thickener, gelling agent, abrasive, lubricant, hydrogen peroxide and solvent, and mixtures thereof. When formulating powdered compositions containing the clathrates, urea peroxide in an amount up to about 35% hydrogen peroxide or polyvinyl pyrrolidone peroxide up to about 18% by weight hydrogen peroxide, organosilane quaternaries and abrasive particles may be included with the clathrate. When abrasive particles are used, mixtures or blends thereof are in an amount from about 5 to about 90% by weight. Abrasive particles can be selected from the group consisting of urea, silicas, silicates, metal oxides, metal carbonates, clays, carbides and plastic. Furthermore, with respect to abrasive particles, our earlier U.S. application Ser. No. 11/175,583, entitled, "Surfactant-free Cleansing and Multifunctional Liquid Coating Composition Containing Nonreactive Abrasive Solid Particles and An Organosilane Quaternary Compound and Methods of Using" (Ohlhausen and Ludwig) was directed to nonreactive abrasive particles. However, in the case of the present invention, the clathrate form of the organosilane quat tends to protect it from reactivity with other solid particles. Non-reactive abrasive particles or coated non-reactive particles are preferred and, when employed, have an average size on the order of from about 5 microns to about 6,000 microns.

When the composition is in the form of a slurry, cream, gel or powder, the concentration of the organosilane quat ranges from about 1% to about 5% by weight. When the inventive compositions are used as a liquid concentrate, hydrogen peroxide is in an amount up to about 35% by weight, quaternary compound is in an amount up to about 12.5% by weight, and urea is in an amount up to about 38% by weight. More preferably, when the inventive composition is used as a liquid end-use product, hydrogen peroxide or a complex thereof is in an amount up to about 3% by weight of hydrogen peroxide and the quaternary compound is in an amount up to about 0.33% by weight and urea is in an amount up to about 1% by weight. In such end-use products, where abrasive particles are present, mixtures or blends thereof are in an amount of up to about 35% by weight.

A particular advantage of urea-quaternary clathrates is that they are not reactive with grits that otherwise react with siliconized quats, such as $SiO_2$, and render the composition unfit or economically unsuitable to yield barrier coatings.

In general, in end-use products, the clathrate and other components are formulated in effective amounts for cleansing a surface and for bonding a multifunctional coating onto a surface thereby rendering it (a) water and soil repellent, and (b) antimicrobial. The antimicrobial benefits of the barrier are provided by the hydrocarbon characteristics of the siliconized quat coating bonded to the surface with reference to our U.S. Pat. Nos. 6,432,181, 6,676,733 and 6,994,890. A wide variety of hard, soft or porous surfaces are suitable for treatment with the clathrates of this invention.

The bonding to or coating of a surface with a quat can occur by two mechanisms. First, the methoxy groups attached to the silicone will hydrolyze in water or in contact with surface water to yield SiOH's that are capable of reacting with siliceous surfaces (—SiOH bonds on the surface of glass, tile, etc.) to form a —Si—O—Si—O— bond between the surface and the quat. Secondly, if the surface is non-siliceous or does not have —OH bondable sites, then the hydrolyzed —SiOH groups from other quat molecules can react and polymerize to form a durable "paint-like" crosslinked —O—Si—O—Si—O—Si—O— etc. coating on the surface. Surfaces like textile fibers such as cotton, cellulose acetate, polyesters, nylon, wool, rayon acrylon, etc.; organic surfaces such as paint films, polystyrene, silicone polymers, wood, rubber, etc. and inorganic surfaces such as silica, sand, glass, concrete and masonry surfaces, etc. can be coated and demonstrate antimicrobial activity. The long chain of the quat is oriented perpendicular to the surface and, when molecules are packed together from one molecule to another with the proper structure, the quat can leave the surface biologically active, water repellent and/or smooth (lubricating).

Methods of Preparing Clathrates of Organosilane Quats

The clathrates of the present invention may be prepared by several methods for urea adduct formation. For example, they may be prepared by a crystallization method where one part of the quat molecule is mixed with three parts of urea in the presence of a solvent or combination of solvents such as methanol ethanol, isopropanol, acetone and benzene, then heated until the mixture becomes homogeneous, followed by cooling and crystallization of the clathrate compound. The clathrate compound is then separated from the remaining solution by filtration, or other suitable means, and dried. After drying, the clathrate compound is a free-flowing, non-caking particulate solid.

An alternative method for preparing the clathrates is a dry mix method. This method has the advantage that the crystallization solvent is eliminated and there is no loss of uncomplexed quat, solvent or urea, which is recycled with the crystallization method. In the dry mix method, urea solids are intensively mixed directly with the quat at room temperature or at an elevated temperature in the absence of any solvent.

The mixture becomes pasty or a solid as the complex formation proceeds. The solid clathrate can then be ground to the desired particle size. Wetting of the mixture with a small amount of solvent can accelerate and augment the adduct formation. Again, the weight ratio is 3 parts urea to 1 part quat.

Another method of preparation is known as the concentration method and merely involves the removal of solvent, as employed in the crystallization method, by evaporation or distillation during complex formation. For example, one part of quat and three parts of urea are dissolved in methanol at reflux. The methanol is completely removed by evaporation or vacuum distillation leaving the clathrate as the residue.

The formation of the urea adducts may be verified by infrared analysis and nitrogen analysis of the product. The infrared analysis is conducted in accordance with the procedure described in "Infrared Absorption Spectra of Some Urea Inclusion Compounds", J. Chem. Soc., 1962, 2340.

The organosilane quats of the following Examples may be defined by the following formula:

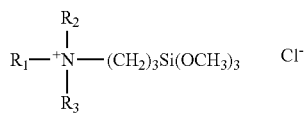

EXAMPLES 1-7 water without urea. In clathrate form with organosilane quats, when solubilized in water, or water and alcohol, the resulting composition is likewise more surface active and provides improved cleaning and bonding of the organosilane quat to the surface than would the same level of organosilane quat in water without urea.

Urea in its solid form, as a powder, granule, pellet, crystal, flake or prill, is abrasive. Surprisingly, this abrasive property significantly aids in the removal of various types of organic and inorganic soil without scratching the surface, particularly when the urea is moistened, even if only slightly moistened. Even more surprising, the powdered clathrate of urea-organosilane quaternary not only cleans the surface as a mild abrasive, but simultaneously imparts a water, soil and stain repellent barrier coating with improved bonding, owing, we believe, to a synergistic combination of the surface tension reducing and abrasive attributes of the mixture. As stated above, a still further benefit of the invention is the finding that, unlike the water-insoluble nature of the broad range of mineral abrasives typically employed in cleansers, the urea-type abrasive is 100% water soluble and, thus, easily and quickly rinsed off the cleaned surface without leaving a gritty residue and without adding water insoluble particles to the wastewater system.

When formulated as liquids with water or solvent, the active organosilane quat is released. The resulting composition may contain hydrogen peroxide to improve bonding of the barrier coating to the surface, thickeners to provide thixotropic, shelf-stable creams and gels and lubricants to facilitate the breakup and removal of the soil that is now no longer

TABLE 1

Organosilane Quaternary-Urea Clathrate Compositions

| | Example | | | | | | |
|---|---|---|---|---|---|---|---|
| | 1 | 2 | 3 | 4 | 5 | 6 | 7 |
| $R_1$ | $C_{18}H_{37}$ | $C_{12}H_{25}$ | $C_{22}H_{45}$ | $C_{12}H_{25}$ | $C_{18}H_{35}$* | $C_{18}H_{35}$* | $C_{18}H_{37}$ |
| $R_2$ | $CH_3$ | $CH_3$ | $CH_3$ | $CH_3$ | H | $CH_3$ | $CH_3$ |
| $R_3$ | $CH_3$ | $CH_3$ | $CH_3$ | $CH_3$ | H | $CH_3$ | $CH_3$ |
| Method of Preparation | Concentration | Concentration | Concentration | Dry Mix | Crystallization | Crystallization | Dry Mix |

*oleyl

The above formula and Table represent a number of clathrate compositions of this invention that have been prepared by the concentration, dry mix or crystallization techniques described above.

Methods of Use

When used in the dry form with sufficient moisture to activate the quat, the inventive clathrate compositions cleanse a surface of insoluble soil, i.e., salts, pollutants, minerals, soap scum, hard water film, foodstuff, rust, mold, mildew, virus and bacteria, and provide the surface with a bonded multifunctional barrier coating to reduce the adhesion and buildup of such soil and microorganisms for easier cleaning.

Upon release of the monomeric organosilane quaternary ammonium compound from the clathrate form, it facilitates the cleaning of the surface and concurrently bonds the organosilane quat to provide a water and soil repellent coating.

The released urea is readily and completely water soluble. When so solubilized, it lowers the surface tension of water and allows the water-urea composition to better penetrate a wide range of organic and inorganic soil on surfaces than attached to the surface. The components are used in effective amounts in aqueous media as slurries, creams or gels for cleansing a surface and for bonding a multifunctional barrier coating onto said surface thereby rendering it water, soil and stain repellent to reduce (a) the adhesion and buildup of hard water minerals, soap scum, foodstuffs and the like, and (b) the attachment and growth of bacteria, virus and fungi.

Thus, the storage-stable clathrate functions in cleaning, cleansing and coating compositions with unique properties which enable a surface to be cleaned or cleansed of insoluble soil and simultaneously rendered water, soil and germ repellent. These properties enable cleansing and coating exterior windows soiled by rain, lake or ocean spray and ground sprinkler spray and/or pollution by dust, exhausts and smokestack emissions. Also, a broad range of interior surfaces that have been soiled with everyday spills and splatters of household soil that result from cooking, eating, washing, etc., may be simultaneously cleaned and provided with a bonded coating that durably repels water and future soiling while having antimicrobial properties.

As stated above, it is surprising that a clathrate of urea and an organosilane quat could be formed, taking into consideration the structural characteristics of the quats, such that storage stability could be achieved. Furthermore, the advantages of our earlier compositional discoveries, with reference to our U.S. Pat. Nos. 6,432,181, 6,676,733 and 6,994,890; U.S. Pat. Publ. No. 2006/0110348; and U.S. application Ser. No, 11/175,583 (filed Jul. 6, 2005), can still be achieved by blending the clathrates with other additives. For example, a barrier coating could be formed and bonded to a surface in situ all the while abrasive solid particles and the clathrate urea-quat are being wiped and massaged across/on the surface in a grinding action in the presence of moisture to remove the insoluble soil. The inventive clathrate composition can also contain the combination of abrasive solid particles and hydrogen peroxide components to provide improved bonding and durability of the barrier coating on various surfaces.

In general, the abrasive solid particles are selected on the basis of their hardness, sizes, structure and reactivity with the organosilane quaternary compound as well as stability with hydrogen peroxide. Compositions of this invention can be formulated as an aqueous slurry, cream or gel. The cleansing and coating compositions may further contain thickeners and/or lubricants such as hydroxypropylcellulose, acrylic polymers, isopropyl myristate, mineral oil and the like. Further, preferably the aqueous media has a pH on the order of about 2 to about 9. The aqueous compositions are also preferably formulated with deionized water.

In accordance with the methods of use, everyday surfaces as found in homes, hotels, offices, stores, autos, ships, airplanes, etc., are treated with a composition that provides a cleansed surface and a multifunctional coating. For example, everyday surfaces that are soiled by the buildup of insoluble water spots, hard water film and minerals that results from rain, lake, ocean and sprinkler spray and the insoluble soap scum, limescale, stains and foodstuff that results from the spills and splatters from cooking, eating, washing, etc. may be cleansed and provided with the multifunctional coating upon application of the inventive composition. For example, a preferred slurry, cream or gel of the clathrate composition can be applied by wiping and massaging onto a soiled surface in an effective amount to break up and loosen the soil which is removed by rinsing and then wiping the surface until it is dry. Upon such application, the surface is cleansed and a multifunctional polymeric coating is formed and bonded onto the surface thereby providing an invisible, water, soil and stain repellent siliconized hydrocarbon barrier coating on which bacteria, virus, mold and mildew will not attach and grow and which restricts the formation, adhesion and buildup of hard water minerals, soap scum, foodstuff and stains for easier cleaning with water or non-abrasive aqueous cleaners.

The invention may be more readily understood consistent with our earlier U.S. Pat. Nos. 6,432,181, 6,676,733 and 6,994,890; U.S. Pat. Publ. No. 2006/0110348; and U.S. application Ser. No. 11/175,583 (filed Jul. 6, 2005), which are incorporated by reference herein in their entireties, by the following detailed disclosure of examples or preferred embodiments of the invention. It is to be understood that the terminology used herein is for the purpose of describing particular embodiments and is not intended to be limiting. For the purpose of a clear understanding, the following terms, as used herein, are defined:

"abrasion resistant" refers to a surface, surface coating or finish that is resistant to damage or removal by washing, scraping or scrubbing with a mildly abrasive substance or process without visibly damaging the surface or finish, as in scratching or blemishing the surface.

"abrasive" or "abrasion" means any material or substance used for grinding or polishing, and the spot or area on a surface that results from being ground, rubbed, agitated or massaged with abrasive "particle(s)" or "grit(s)".

"antimicrobial" means the ability of a surface and its coating to resist the attachment and growth of microorganisms, particularly those that are disease-causing.

"application", "applying" or "applied" as used herein means the treatment of a surface with the clathrate composition either in a granular or liquid form, usually in the form of a liquid, slurry, cream or gel.

"bacteria" means ubiquitous one-celled organisms that appear singly or in chains and are comprised of various species involved in fermentation, putrefaction and infectious diseases.

"bond", "bonded" or "bondable" means the ability to strongly adhere the composition to the surface, as in the ability to bond a water and soil repellent finish, coating or characteristic to an otherwise water and soil accepting surface. As used herein, the composition is deemed "bonded" or "bondable" when it is resistant to removal by concentrated sulfuric acid and 50% sodium hydroxide, or any soap, solvent, detergent, abrasive-type cleanser that would not stain, blemish or damage an untreated form of the same surface.

"clathrate(s)", as used herein, means an inclusion complex(s). In one form of the complex, the molecules of the quat are completely enclosed within the urea, but without chemical interaction. Urea clathrates are inclusion complexes of the channel or canal type. The complexing urea solids wrap around the rather straight-chain hydrocarbon group of the organosilane quat. In another form, the inclusion complex is an unbonded association of the organosilane quat fully or partly locked within the crystal lattice of urea. As used herein, therefore, "clathrate(s)" is meant to include any of such type inclusion complexes where the urea and organosilane quaternary ammonium compound are associated with one another in an unbonded form such that they may provide the benefits of this invention including storage-stable solids, free from handling and shipping hazards, and non-flammability.

"clean", "cleansed", "cleanser" and "cleansing" either refer to surfaces that are unsoiled, unstained and free form soil buildup, or the liquid cleansing/coating composition of this invention and the methods of using them.

"disinfectant" or "disinfecting" means any chemical agent used chiefly on inanimate surfaces to destroy or inhibit the growth of harmful organisms (germs).

"durable" or "durability" means long-lasting and not easily removed by washing and/or wiping using plain (tap) water, soap solutions, detergent solutions, household solvents, mildly abrasive (non-damaging) cleansers or conventional cleaner/degreasers.

"everyday household soil" means the spills, splatters and blemishes on a surface that result from cooking, eating, drinking, washing, bathing and showering such as milk, coffee, teas, juices, sauces, gravies, food boil over, soap scum, water spots, mineral deposits, etc.

"everyday surfaces" means the full range of surfaces in homes, offices, factories, public buildings and facilities, vehicles, aircraft and ships, and the like.

"everyday vehicular soil" means the spills, splatters and blemishes on the exterior of a vehicular surface that result from rain, sleet, snow, insects, mud and road grime, and on the interior of a vehicular surface that result from fingerprints, food spillage, plasticizer leaching, smoking, use of hair and deodorizing sprays and air circulation.

"germ(s)" means disease-producing microorganisms.

"insoluble soil", "soil", and "water and oil insoluble soil" mean surface soil and stains that cannot be effectively solubilized and removed by washing with water, soaps, solvents and detergents and which can be removed by grinding or polishing the surface with the solid granular or liquid compositions formed by the clathrate of this invention.

"liquid(s)" as it applies to compositions of this invention means they have the ability to flow, a property largely dependent on their viscosity.

"massaging" refers to wiping and/or scrubbing the granular clathrate or liquid cleansing and coating composition on and into the buildup until the soil is no longer attached to the surface.

"microorganism(s)" means any organism too small to be viewed by the unaided eye, such as bacteria, protozoa, virus and some fungi and algae.

"mitigate" means to lessen in force or intensity and make less severe; to mollify and control; particularly with respect to the attachment and growth of microorganisms.

"mold" and "mildew" mean the growth of minute fungi that forms on animate and inanimate surfaces and is generally associated with dampness and/or decay.

"monomer" or "monomeric" means a molecule capable of reacting with identical or different molecules to form a compound or a polymer.

"multifunctional" means the process of achieving two or more discernable results from a single application, as in simultaneously or sequentially cleaning and coating a surface whereby the coating also performs the function(s) of rendering the surface water repellent, soil repellent and/or antimicrobial "nonreactive" refers to abrasive solid particles that do not react with the organosilane quaternary or hydrogen peroxide so as to diminish their cleansing and coating proportions in accordance with this invention; or, if reactive in their normal state, are coated with a variety of substances that form a barrier to make them nonreactive and storage-stable to provide the desired surface cleansing and bonding functions.

"particle(s) and "grit(s)" mean minute pieces of fragments of solids with varying hardness, structure, texture and size used for the removal of insoluble soil.

"polymer" or "polymeric" means a compound of high molecular weight usually derived by the reaction/'condensation of many smaller molecules.

"repel" or "repellent" means to resist effectively, to keep off or out, to fail to mix with and to resist the absorption, attachment or passage of water, soil and germs.

"resistant to removal" means a coating or surface finish that is not easily removed by washing or cleaning with conventional soaps, solvents, detergents, mildly abrasive cleansers or cleaner/degreasers that would not otherwise etch or damage an untreated surface of the same composition and construction.

"sanitizer" or "sanitizing" means a substance, preparation or process for cleaning a surface to render it free from dirt, soil, germs, etc.

"soil repellent" means a surface that exhibits reduced adhesion to, and buildup of, for example, everyday household and vehicular soil both before and after evaporation of the water component.

"sterilant" or "sterilization" means any chemical agent, substance or process that causes the destruction of at least 99.9% of living microorganisms, "storage-stable" refers to a useful shelf life of the granular or solid clathrates, or their diluted liquid compositional form when stored in containers under ambient environmental conditions of temperature as found in warehouses, shipping containers, packages, etc., up to 120° F. for months, typically desired for more than six months or at least one year.

"surface(s)" means the full range of hard or soft surfaces, whether porous or non-porous, siliceous or non-siliceous, as exemplified by everyday surfaces such as those used in the following examples which illustrate the compositions and methods of this invention. Examples of such surfaces include, without limitation metal, glass, plastics, rubber, porcelain, ceramic, marble, granite, cement, tile, grout, silica, enameled appliances, polyurethane, polyester, polyacrylic, melamine/phenolic resins, polycarbonate, siliceous, painted surfaces, wood, and the like.

"surfactant" and "surfactant-free" refer to a substance that reduces surface tension or interfacial tension between two liquids or a liquid and solid as listed in the Stepan Company, Northfield, Ill., 2004 "Global Product Catalog". It includes detergents, wetting agents and emulsifiers. The terms are meant to exclude an organosilane quaternary ammonium compound and the surface-tension reducing properties of the types used in this invention.

"virus" means an ultramicroscopic, metabolically inert infectious agent that replicates only within the cells of living hosts, mainly bacteria, plants and animals, but which are transferred by hand and body contact directly or indirectly through hand and body contact surfaces.

"water repellent" and "water repellency" as used herein describe the hydrophobic nature of characteristic of a surface and its ability to repel water as measured by visual observation. It may also be measured by the contact angle of a drop or droplet of distilled water on the surface. (Contact angles measured with rainwater, municipally furnished tap water, or ground water are typically more variable and non-reproducible, and commonly measure up to 10° less than those using distilled or de-ionized water.) Generally, the hydrophobicity of a discrete surface is rated in terms of its contact angle to water drops as follows:

| | |
|---|---|
| Excellent | Compact drops, well rounded, with bright sparkles measuring 95° or more |
| Good | Less rounded drops, but bright sparkles that exhibit slight spread, measuring 85° to 95° |
| Fair | Visible flattening of the water drops, measuring 70° to 85° |
| Poor | Relatively flat water drops, exhibiting more spread of the water and measuring 50° to 70°. |

Preparation for Test Surfaces

All test surfaces were cleaned by scrubbing the surface with "Miracle Scrub", a non-scratching abrasive hard surface cleanser available from Unelko Corporation, Scottsdale, Ariz., and using a moist cellulose sponge. After cleaning, the surface was rinsed with hot water to remove the Miracle Scrub excess, followed by a rinse with deionized water (a clean surface can be noted when the water spreads and wets the surface) followed by drying with a paper towel. The cleaned surface was allowed to air dry at least one hour at room temperature prior to application of the clathrates.

Formation, Adhesion and Buildup of Insoluble Soils On the Test Surfaces

Hard water mineral deposits: Hard water spots were formed by spraying Scottsdale, Ariz. (hard) tap water onto the test surface in a horizontal position and allowing the water to evaporate, leaving hard water spots on the surface. The procedure was repeated until a substantial hard water spot residue remained on the test surface.

Soap scum: An aqueous solution of "Ivory Soap" (Procter and Gamble), in Scottsdale, Ariz.'s hared water, was sprayed onto the hard water mineral deposit test surface in a horizontal position and the water allowed to evaporate, leaving a soap scum soil on the surface. The procedure was repeated until a substantial soap scum soil residue remained on the test surface. The soiled test surface (hard water spots and soap scum) was then placed in a 250° F. oven for one hour to drive off any residual water from the surface.

Grease: "Crisco" spray (canola and soybean oils) was applied to the dried test surface in a horizontal position until a substantial layer of grease residue remained on the test surface. The soiled test surface was then placed in a 400° F. oven for one hour at which time the grease had begun to turn brown from slight charring.

Testing of Urea Clathrates of Organosilane Quaternary Compounds

A. Testing of the Clathrate Compositions of this Invention on Glass to Form a Barrier Coating Which is Water and Stain Repellent:

A glass mirror was cleaned with an abrasive cleaner such as Miracle Scrub as described above. A paper towel was folded into a two inch by five inch applicator. One end of the applicator was sprayed with water to wet the towel. A small amount of the solid clathrate composition was sprinkled on the water moistened towel and then applied to the surface of the mirror with a circular overlapping rubbing motion. The treated surface was then rinsed with water and dried with a paper towel. The treated surface was then tested for the presence of the hydrophobic barrier coating.

Water Repellent: The treated surface was sprayed with water and the beading of the water droplets observed. If the barrier coating was present, the water droplets bead and do not spread like on the untreated portion of the surface.

Stain Repellent: A yellow Hi-Liter Marker by Avery, made in Mexico, will be repelled by the barrier coating (RYMM or Repells Yellow Magic Marker) but will not be repelled by the untreated surface.

B. Clean and Shield Coating Test of Cleansers Based on Clathrates of this Invention and their Storage Stability A glass mirror was cleaned as per the above procedure. A black permanent Magic Marker (i.e., Marks-A-Lot by Avery) was used to coat the mirror with black stains for testing the cleanser for the ease of removal and simultaneous formation of the barrier coating.

Application of the cleanser to the mirror surface was performed as per the above procedure. The excess cleanser (grit) was removed from the mirror surface with a water rinse and agitated with a paper towel followed by drying with a paper towel. The treated surface was then tested for the presence of the barrier coating as per the above for water repellency and stain repellency.

Stain Removal: The treated surface was examined for removal of the black stain by observing any residual. Complete removal of the stain was required to pass the test.

Storage Stability: It is known that organosilane quaternary compounds will react with siliceous surfaces (See our pending application, U.S. Ser. No. 11/175,583, filed Jul. 6, 2005). However, clathrates of organosilane quaternary compounds make the quaternary compounds unavailable for reaction with siliceous surfaces until released from the clathrate, for example, by solution of the urea. To demonstrate the stability of the clathrate of this invention, the clathrate of octadecylaminodimethyltrimethoxysilylpropyl ammonium chloride was mixed with silicon dioxide and stored at ambient laboratory conditions for 22 months and evaluated as a water and stain repellent, clean and shield composition with stain removal.

EXAMPLES 8-12

The clathrates of Examples 1-7 were tested for water and stain repellency according to the above procedures. All these clathrates passed the tests.

EXAMPLES 13-16

Clathrate storage stability and performance were tested according to the above tests and the results are reported in Table 2.

TABLE 2

Clathrate* Cleanser Storage Stability and Performance

| | EXAMPLE | | | |
|---|---|---|---|---|
| | 13 | 14 | 15 | 16 |
| % SiO$_2$** | 96.8 | 93.6 | 87.2 | 74.4 |
| % Clathrate | 3.2 | 6.4 | 12.8 | 25.6 |
| (% Quat) | (0.8) | (1.8) | (3.6) | (7.2) |
| INITIAL: | | | | |
| Water Repellent | Yes | Yes | Yes | Yes |
| Stain Repellent | Yes | Yes | Yes | Yes |
| Stain Removal | Complete | Complete | Complete | Complete |
| AFTER 22 MOS. STORAGE: | | | | |
| Water Repellent | Yes | Yes | Yes | Yes |
| Stain Repellent | Yes | Yes | Yes | Yes |
| Stain Removal | Complete | Complete | Complete | Complete |

*Urea Clathrate of Octadecylaminodimethyltrimethoxysilylpropyl ammonium chloride
**Silcosil 53, U.S. Silica C. Preparation and Testing of Spray and Wipe Cleaners from Urea Clathrates of Organosilane Quaternary Compounds Clean and shield compositions were prepared by dissolving 6.4 gms of each urea clathrate of Examples 4 and 7 from Table 1 in 800 ml of deionized water (pH=3) by shaking in a plastic bottle. The resulting solutions contained 0.2% organosilane quaternary compound and 0.6% urea. Both solutions were clear and foamed on shaking.

The cleaning compositions were each sprayed on a clean glass surface area and wiped up with a paper towel until the surface was dry and polished. Both treated surfaces were then evaluated and found to be water repellent and stain repellent.

However, in similar compositions containing urea peroxide as a solid component to supply hydrogen peroxide as a surface cleaner, biocide and a synergistic bonding agent in combination with siliconized quaternary compounds (Ref: U.S. Pat. No. 6,994,890) the long term stability of the composition was compromised after 19 months. It is believed that the urea peroxide is hygroscopic and the moisture adsorbed caused the clathrate to decompose releasing the siliconized quaternary compound which reacted with the silicone dioxide grit which then prevented the desired barrier coating to be formed when the aged composition was applied to the surface to be treated. However, if there is a high level of the siliconized quaternary compound in the cleanser composition it remains stable and functional in the presence of the silicone dioxide grit over a period of time and enable the creation of the barrier coating with the excess quaternary compound available as demonstrated in Table 2.

Additional studies of cleaners containing grits which are believed to be chemically inert to the siliconized quaternary compounds and the clathrates derived from them, in the presence of urea peroxide, are reported in Table 3. All cleansers perform satisfactorily on the water repellency, stain repellency and stain removal tests.

Another study employing the same grits and clathrates but employing polyvinylpyrrolidone (PVP)-hydrogen peroxide polymer complexes (a solid, containing about 18.5% hydrogen peroxide) as the hydrogen peroxide source, were prepared and subjected to performance testing as reported in Table 4. All of the cleansers performed satisfactorily but those containing the PVP polymer were a bit difficult to spread and remove due to their thickening when employed with a limited amount of water in the tests.

EXAMPLES 17-22

TABLE 3

Cleansers Containing Siliconized Quaternary Clathrates, Non-Reactive Grits and Urea Peroxide

| | EXAMPLE | | | | | |
|---|---|---|---|---|---|---|
| | 17 | 18 | 19 | 20 | 21 | 22 |
| Grit | NYCO | W-610 Ceramic Spheres | Mica 3X | Hydrated $AL_2O_3$ OC 1500 | NP15 Polypropylene | A2-325 $AL_2O_3$ |
| | Wollastonite | 3M | H. M. Royal | Almatis | Eastman | Almatis |
| Clathrate | Example 7 | Example 7 | Example 7 | Example 4 | Example 4 | Example 4 |
| BARRIER COATING: | | | | | | |
| Water Repellent | Yes | Yes | Yes | Yes | Less | Yes |
| Stain Repellent | Yes | Yes | Yes | Yes | Yes | Yes |
| Stain Removal | Yes | Yes | Yes | Yes | Yes | Yes |

Cleanser Formulas:
Grit 89.83%
Urea Peroxide 8.57% (3% $H_2O_2$)
Clathrate 1.60% (0.4% Quat)

EXAMPLES 23-28

TABLE 4

Cleansers Containing Siliconized Quaternary Clathrates, Non-Reactive Grits and PVP $H_2O_2$

| | EXAMPLE | | | | | |
|---|---|---|---|---|---|---|
| | 23 | 24 | 25 | 26 | 27 | 28 |
| Grit | NYCO | W-610 Ceramic Spheres | Mica 3X | Hydrated $AL_2O_3$ OC 1500 | NP15 Polypropylene | A2-325 $AL_2O_3$ |
| | Wollastonite | 3M | H. M. Royal | Almatis | Eastman | Almatis |
| Clathrate | Example 7 | Example 7 | Example 7 | Example 4 | Example 4 | Example 4 |
| BARRIER COATING: | | | | | | |
| Water Repellent | Yes | Yes | Yes | Yes | Yes | Yes |
| Stain Repellent | Yes | Yes | Yes | Yes | Yes | Yes |
| Stain Removal | Yes | Yes | Yes | Yes | Difficult | Yes |

Cleanser Formulas:
Grit 82.2%
PVP $H_2O_2$ 16.2% (3% $H_2O_2$)
Clathrate 1.60% (0.4% Quat)

D. Preparation and Testing of Cleansers from Urea Clathrates and Urea Grit

Urea prills were ground to a fine powder on a Waring Blender to a particle size of up to about 6,000 microns. However, particles size was not considered to be a critical feature of the clathrate solids or solid diluents, like urea. According to this invention, urea, or other solids, are in the form of prills, granules, powder, flakes, pellets or crystals at various particle sizes to achieve the objectives of this invention. The urea clathrate of 3-(trimethoxysilyl)propyldimethyloctadecyl ammonium chloride (Example 7, Table 1) was ground to a fine powder in the Waring Blender having a particle size less than about 1,000 microns. A powder blend of the urea powder and the clathrate powder was then prepared by weighing the amounts indicated in Table 5 into a glass jar, sealing the jar and shaking vigorously.

Application of the powder to the test surface was done by sprinkling the blend onto the test surface followed by rubbing the cleanser on the test surface with a moistened paper towel with a circular overlapping motion. The treated surface was then rinsed with water and dried with a paper towel. The treated surface was then evaluated for the removal of stains, soap scum, water spots, and grease, and the formation of a barrier coating.

EXAMPLES 29-31

TABLE 5

Preparation and Testing of Cleansers from Urea Clathrates and Urea Grit

| | EXAMPLE | | |
|---|---|---|---|
| | 29 | 30 | 31 |
| Grams Urea | 100 | 100 | 100 |
| Grams Clathrate | 0.40 | 2.0 | 4.0 |
| (Grams Quat) | (0.10) | (0.50) | (1.0) |
| (% Quat) | (0.0996) | (0.4902) | (0.962) |
| Water Repellent | Yes | Yes | Yes |
| Stain Repellent | Yes | Yes | Yes |
| Stain Removal | Yes | Yes | Yes |
| Water Spot Removal | Yes | Yes | Yes |
| Soap Scum Removal | Yes | Yes | Yes |
| Barrier Coating Applied | Yes | Yes | Yes |
| Grease Removal | Yes | Yes | Yes |
| Barrier Coating Applied | Yes* | Yes | Yes |

*Required two applications

Conclusion: All cleanser compositions employing urea as the grit and the organosilane quat clathrate as the barrier coating composition as presented in Table 5, gave satisfactory cleanser performance and deposited the water and stain repellent barrier coating.

E. Determination of the Stability of Organosilane Quaternary Compounds Against Decomposition by Solvents The following experiments were conducted to determine if the clathrate compositions of this invention would be decomposed by chloroform (a strong solvent).

Solubility of Urea in Chloroform 7.51 grams of urea were slurried in a beaker with 75.4 grams of chloroform by magnetic stirring for 10 minutes. The slurry was then filtered by gravity through filter paper. The filtrate was employed to rinse the beaker to remove all solids and the rinse added to the filter cake. The filtrate was then evaporated in a tared beaker and a residue of 0.01 grams obtained (which was within experimental error). From this experiment, it can be concluded that urea was insoluble in chloroform.

Solubility of Organosilane Quaternary Clathrates in Chloroform 10.21 grams of Example 7, Table 1 organosilane quaternary clathrate was slurried as above in 75 grams of chloroform for 10 minutes and the slurry filtered as above and the filtrate evaporated to dryness. A waxy residue of 0.07 grams remained in the beaker. The residue had an odor of chloropropyltrimethoxysilane (a starting material for the preparation of the organosilane quaternaries) and when applied to a clean glass surface with a paper towel showed water and stain repellency but was removed easily with Miracle Scrub.

It can be concluded that this residue was not the organosilane quaternary. The solids that were filtered were dried to constant weight. 10.24 grams were recovered. 10.21 grams of the clathrate had been added. The difference of +0.03 grams was within experimental error. It can be concluded that the clathrate was not soluble in chloroform and that the organosilane quaternary was not extracted from the clathrate by the chloroform. This further demonstrates the remarkable stability of the clathrates of this invention.

Those of ordinary skill in the art realize that the descriptions, procedures, methods and compositions presented above can be revised or modified without deviating from the scope of the described embodiments, and such do not depart from the scope of the invention.

What is claimed is:

1. A storage-stable particulate solid clathrate of urea and an organosilane quaternary ammonium compound.

2. The clathrate of claim 1 wherein said organosilane quaternary ammonium compound has at least one linear chain length of at least 10 carbon atoms.

3. The clathrate of claim 2 wherein said linear hydrocarbon chain length is from 10 to 22 carbons.

4. The clathrate of claim 1 wherein said organosilane quaternary ammonium compound has a $C_{10}$-$C_{22}$ saturated or unsaturated hydrocarbon group.

5. The clathrate of claim 1 wherein said organosilane quaternary ammonium compound is defined by the formula:

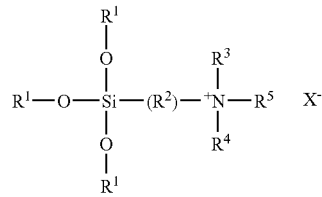

Wherein $R^1$=hydrogen and/or $C_1$ to $C_4$ alkyl; $R^2$=divalent hydrocarbon radical with $C_1$ to $C_8$ carbon atoms, $R^3$=hydrogen or C, to $C_4$ alkyl, $R^4$=hydrogen or $C_1$ to $C_{10}$ alkyl, $R^5$=$C_{10}$ to $C_{22}$ saturated or unsaturated hydrocarbon radical and X=halide, carboxylate, sulfonate, hydroxide, sulfate, or phosphate.

6. The clathrate of claim 1 wherein said organosilane quaternary ammonium compound is selected from the group consisting of
  3-(trimethoxysilyl)propyldimethyloctadecyl ammonium chloride,
  3-(trimethoxysilyl)propyldidecylmethyl ammonium chloride,
  3-(trimethoxysilyl)propyltetradecyldimethyl ammonium chloride,
  3-(trimethoxysilyl)propyldimethylsoya ammonium chloride,
  3-(trimethoxysilyl)propyldimethyloleyl ammonium chloride,
  3-(trimethoxysilyl)propyloctadecyl ammonium chloride,
  3-(trimethoxysilyl)propyloleyl ammonium chloride,
  3-(trihydroxysilyl)propyldimethyloctadecyl ammonium chloride, and
  3-(trimethoxysilyl)propyldocosane ammonium chloride.

7. The clathrate of claim 1 wherein said organosilane quaternary ammonium compound is present in an amount of up to about 25% by weight of said clathrate.

8. The clathrate of claim 7 and a diluent wherein said organosilane quaternary ammonium compound is present in an amount of from about 0.01% to about 25% by total weight of said clathrate and diluent.

9. The clathrate of claim 1 and a diluent selected from the group consisting of water and an alcohol, and mixtures thereof.

10. The composition of claim 9 as a liquid end-use product wherein said organosilane quaternary ammonium compound is present in a concentration of about 0.01% to about 1% by weight based on the total weight of said clathrate and diluent.

11. The clathrate of claim 1 and a diluent to form a slurry, cream, gel or powder, wherein said organosilane quaternary ammonium compound is present in a concentration of about 1% to about 5% by weight based on the total weight of said clathrate and diluent.

12. The composition of claim 9 as a storage-stable cleansing and multifunctional coating composition for treating a surface thereby rendering it water and soil repellant.

13. The composition of claim 9 containing abrasive particles.

14. The composition of claim 13 in the form of a slurry, cream or gel.

15. The clathrate of claim 1 and an additive selected from the group consisting of additional urea, surfactant, thickener, gelling agent, abrasive, lubricant, additional urea peroxide, polyvinyl pyrrolidone peroxide, propylene glycol and solvent, and mixtures thereof.

16. The composition of claim 9 containing hydrogen peroxide or a complex thereof.

17. The composition of claim 16 as a liquid concentrate wherein hydrogen peroxide is in an amount up to about 30% by weight, said quaternary ammonium compound is in an amount up to about 12.5% by weight and urea is in an amount up to about 38% by weight.

18. The composition of claim 16, as a liquid end-use product, wherein said hydrogen peroxide or complex thereof is in an amount of up to about 3% by weight of hydrogen peroxide and said quaternary ammonium compound is in an amount up to about 0.33% by weight and urea is in an amount up to about 1% by weight.

19. The composition of claim 9 wherein abrasive particles are in an amount up to about 35% by weight.

20. The composition of claim 19 wherein said abrasive particles are selected from the group consisting of additional urea, silicas, silicates, metal oxides, metal carbonates, clays, carbides, and plastics.

21. The composition of claim 20 wherein said abrasive particles have an average size on the order of from about 5 microns to about 6,000 microns.

22. The composition of claim 1 wherein said urea and organosilane quaternary ammonium compound are in effective cleansing and bonding amounts for cleansing a surface and for bonding a multifunctional coating onto said surface thereby rendering it (a) water and soil repellant and (b) antimicrobial.

23. The composition of claim 12 wherein said surface is siliceous, plastic, metal, cementicious, wood, marble, granite, fabric or skin.

24. The clathrate of claim 1 and additional urea as a diluent for said clathrate.

25. The composition of claim 24 as an end-use product wherein said organosilane quaternary ammonium compound is present in a concentration of about 0.01% to about 1% by weight based on the total weight of said clathrate and additional urea diluent.

26. The composition of claim 24 as a slurry, cream, gel or powder, wherein said organosilane quaternary ammonium compound is present in a concentration of about 1% to about 5% by weight based on the total weight of said clathrate and additional urea diluent.

27. The composition of claim 24 as a storage-stable cleansing and multifunctional coating composition for treating a surface thereby rendering it water and soil repellent.

28. The composition of claim 24 wherein said additional urea diluent is in the form of abrasive particles.

29. The composition of claim 28 in the form of a slurry, cream, gel or powder.

30. The composition of claim 24 containing an additive selected from the group consisting of a surfactant, thickener, gelling agent, abrasive, lubricant, additional urea peroxide, polyvinyl pyrrolidone peroxide, propylene glycol, and solvent, and mixtures thereof.

31. The composition of claim 24 containing hydrogen peroxide or a complex thereof.

32. The composition of claim 31 as a liquid concentrate wherein hydrogen peroxide is in an amount up to about 30% by weight, said quaternary ammonium compound is in an amount up to about 12.5% by weight and urea is in an amount up to about 38% by weight.

33. The composition of claim 31 as a liquid end-use product wherein said hydrogen peroxide or complex thereof is in an amount of up to about 3% by weight of hydrogen peroxide and said quaternary ammonium compound is in an amount up to about 0.33% by weight and urea is in an amount up to about 1% by weight.

34. The composition of claim 24 wherein abrasive particles are in an amount up to about 35% by weight.

35. The composition of claim 34 wherein said abrasive particles are selected from the group consisting of additional urea, silicas, silicates, metal oxides, metal carbonates, clays, carbides, and plastics.

36. The composition of claim 35 wherein said abrasive particles have an average size on the order of from about 5 microns to about 6,000 microns.

37. The composition of claim 24 wherein said urea and organosilane quaternary ammonium compound are in effective cleansing and bonding amounts for cleansing a surface and for bonding a multifunctional coating onto said surface thereby rendering it (a) water and soil repellant and (b) antimicrobial.

38. The composition of claim 24 wherein the additional urea is in the form of prills, granules, powder, flakes, pellets or crystals, and the clathrate is uniformly distributed therein.

39. A method for treating a surface comprising applying to the surface a storage-stable particulate solid clathrate of an organosilane quaternary ammonium compound and urea.

40. The method of claim 39 wherein said organosilane quaternary ammonium compound has at least one linear chain length of at least 10 carbon atoms.

41. The method of claim 39 wherein said linear hydrocarbon chain length is from 10 to 22 carbons.

42. The method of claim 39 wherein said organosilane quaternary ammonium compound has a $C_{10}$-$C_{22}$ saturated or unsaturated hydrocarbon group.

43. The method of claim 39 wherein said clathrate is combined with a diluent to form a composition for treating the surface.

44. The method of claim 39 wherein said diluent is selected from the group consisting of additional urea, water and alcohol, and mixtures thereof.

45. The method of claim 39 for treating a surface thereby rendering it water and soil repellant.

46. The method of claim 45 wherein said organosilane quaternary ammonium compound is selected from the group consisting of
   3-(trimethoxysilyl)propyldimethyloctadecyl ammonium chloride,
   3-(trimethoxysilyl)propyldidecylmethyl ammonium chloride,
   3-(trimethoxysilyl)propyltetradecyldim ethyl ammonium chloride, 3-(trimethoxysilyl)propyldimethylsoya ammonium chloride,
3-(trimethoxysilyl)propyldimethyloleyl ammonium chloride,
3-(trimethoxysilyl)propyloctadecyl ammonium chloride,
3-(trimethoxysilyl)propyloleyl ammonium chloride,
3-(trihydroxysilyl)propyldimethyloctadecyl ammonium chloride, and
3-(trimethoxysilyl)propyldocosane ammonium chloride.

47. The method of claim 43 wherein said organosilane quaternary ammonium compound is present in an amount of about 0.01% to about 25% by weight of the total weight of said clathrate and diluent.

48. The method of claim 47 wherein said composition contains an additive selected from the group consisting of additional urea, surfactant, thickener, gelling agent, abrasive, lubricant, additional urea peroxide, polyvinyl pyrrolidone peroxide, propylene glycol, and solvent, and mixtures thereof.

49. The method of claim 39 wherein the composition contains hydrogen peroxide or a complex thereof.

50. The method of claim 49 wherein the composition contains hydrogen peroxide in an amount up to about 8% by weight, said organosilane quaternary ammonium compound is in an amount up to about 5% by weight and abrasive particles in an amount up to about 35% by weight.

51. The method of claim 50 wherein said hydrogen peroxide or complex thereof is in an amount from about 3 to about 6% by weight of hydrogen peroxide and said organosilane quaternary ammonium compound is in an amount up to about 1% by weight.

52. The method of claim 39 wherein said clathrate is in effective cleansing and bonding amounts for cleansing said surface and for bonding a multifunctional coating onto said surface thereby rendering it (a) water and soil repellant and (b) antimicrobial.

* * * * *